(12) United States Patent
McGrath et al.

(10) Patent No.: US 7,694,569 B2
(45) Date of Patent: Apr. 13, 2010

(54) PHASED ARRAY ULTRASONIC WATER WEDGE APPARATUS

(75) Inventors: Matthew McGrath, Anthem, AZ (US);
David Galbally, Huntersville, NC (US);
Paul Johnson, Iron Station, NC (US);
Trevor Davis, Charlotte, NC (US);
Walter Mitchell, III, Huntersville, NC (US)

(73) Assignee: General Electric Company, Schenectady, NY (US)

( * ) Notice: Subject to any disclaimer, the term of this patent is extended or adjusted under 35 U.S.C. 154(b) by 1574 days.

(21) Appl. No.: 10/925,343

(22) Filed: Aug. 24, 2004

(65) Prior Publication Data

US 2009/0165563 A1    Jul. 2, 2009

(51) Int. Cl.
*G01N 29/04* (2006.01)
*G01N 29/32* (2006.01)

(52) U.S. Cl. .......................................... 73/644; 73/641

(58) Field of Classification Search ................... 73/628, 73/641, 644
See application file for complete search history.

(56) References Cited

U.S. PATENT DOCUMENTS

| | | | |
|---|---|---|---|
| 2,592,134 A | 4/1952 | Firestone | |
| 3,906,780 A | 9/1975 | Baldwin | |
| 3,938,372 A * | 2/1976 | Sproule | 73/633 |
| 4,098,132 A | 7/1978 | Mikesell | |
| 4,455,872 A * | 6/1984 | Kossoff et al. | 73/618 |
| 4,472,975 A * | 9/1984 | Beck et al. | 73/644 |
| 4,966,746 A | 10/1990 | Richardson et al. | |
| 5,009,105 A | 4/1991 | Richardson et al. | |
| 5,156,803 A | 10/1992 | Engding et al. | |
| 5,377,237 A | 12/1994 | Richardson et al. | |
| 5,460,045 A | 10/1995 | Clark et al. | |
| 5,568,527 A | 10/1996 | Richardson et al. | |
| 5,784,425 A | 7/1998 | Morlan | |
| 5,814,731 A | 9/1998 | Alexander et al. | |
| 6,076,407 A | 6/2000 | Levesque et al. | |
| 6,169,776 B1 | 1/2001 | Collins | |
| 6,332,011 B1 | 12/2001 | Johnson | |
| 2003/0233880 A1 | 12/2003 | Siverling et al. | |

FOREIGN PATENT DOCUMENTS

EP    0060952 A2    9/1982

OTHER PUBLICATIONS

Spanish Search Report for application No. 2005802029, published Aug. 12, 2005.
International Search Report; Spanish Office Action; Oct. 28, 2008; 8 pages.

* cited by examiner

*Primary Examiner*—John E Chapman
(74) *Attorney, Agent, or Firm*—Armstrong Teasdale LLP

(57) ABSTRACT

A phased array ultrasonic probe assembly includes, in an exemplary embodiment, a housing and a phased array transducer supported inside the housing. The housing includes a first side wall and an opposing second side wall, and a first end wall and an opposing second end wall. The first and second side walls and the first and second end walls define a housing cavity in which the phased array transducer is positioned. The first and second side walls each have an inside surface that include a plurality of projections.

18 Claims, 4 Drawing Sheets

PHASED ARRAY ULTRASONIC WATER WEDGE APPARATUS

BACKGROUND OF THE INVENTION

This invention relates generally to ultrasonic inspection of dissimilar metal welds, and more particularly ultrasonic inspection of dissimilar metal welds with phased array transducers.

Pipe welds in, for example, nuclear reactors, have been examined with ultrasonic transducers using 45° and 60° refracted longitudinal waves. These angles have been established as the "norm" based on the weld configurations, ultrasonic theory, and field experience. The pipes are raster scanned in four directions to completely examine the weld volume which is very time consuming. Problems are sometimes experienced with the setup of the manipulator that delivers the ultrasonic transducers to the weld, and more importantly with the contact between the transducers and the specimen being examined. If continuous contact between the transducer and the pipe is not maintained, the scan data collected will be flawed which can result in time consuming rescans or missed defect detections.

Phased array ultrasonic probes have been developed that increase examination efficiency of conventional ultrasonic examination techniques by electronically steering the ultrasonic beam through a given range of angles. One major problem that still exists is the contact between the phased array ultrasonic transducer and the specimen being examined. Complex gimbling mechanisms that apply downward pressure on the transducers have been used to attempt to overcome this problem. However, other issues, for example, improper scanner setup and irregularities in the pipe surface can also effect inspection accuracy.

BRIEF DESCRIPTION OF THE INVENTION

In one aspect, a phased array ultrasonic probe assembly is provided that includes a housing and a phased array transducer supported inside the housing. The housing includes a first side wall and an opposing second side wall, and a first end wall and an opposing second end wall. The first and second side walls and the first and second end walls define a housing cavity in which the phased array transducer is positioned. The first and second side walls each have an inside surface that include a plurality of projections.

In another aspect, a phased array ultrasonic probe assembly is provided that includes a housing and a phased array transducer pivotably mounted inside the housing. The phased array transducer includes a plurality of elements. The housing includes a first side wall and an opposing second side wall, and a first end wall and an opposing second end wall. The first and second side walls and the first and second end walls define a housing cavity in which the phased array transducer is positioned. The first and second side walls each have an inside surface that include a plurality of projections.

In another aspect, a method of inspecting a portion of a weld in a metal object using a phased array ultrasonic probe assembly is provided. The probe assembly includes a housing and a phased array transducer pivotably mounted inside the housing. The housing includes a first side wall and an opposing second side wall, and a first end wall and an opposing second end wall. The first and second side walls and the first and second end walls define a housing cavity in which the phased array transducer is positioned. The first and second side walls each have an inside surface that includes a plurality of projections. The method includes positioning the phased array ultrasonic probe assembly adjacent an outer surface of the portion of the weld to be inspected, adding a fluid to the housing cavity, and scanning the weld.

DETAILED DESCRIPTION OF THE INVENTION

A phased array ultrasonic probe assembly that includes a housing and a phased array transducer supported inside the housing is described below in detail. The housing includes opposing side walls having a plurality of "saw tooth" projections, and opposing end walls each having a at least one "saw tooth", or triangle shaped, projection. The housing holds the phased array ultrasonic transducer in a standing column of water. The water fills the volume between the bottom of the transducer and the material that is being examined and permits for the ultrasonic sound waves to travel from the probe directly to the material with no break in contact. Sound exits the transducer at a predetermined angle and travels through the water until it comes in contact with the material where a velocity change is experienced. The change in speed causes the sound to refract as it penetrates that material permitting the weld volume to be inspected using the predetermined angle. To minimize the amount of noise introduced into the system, the walls of the housing are designed to absorb or scatter the near surface reflectors which improves resolution. Both circumferential and axial flaws can be identified. The circumferential flaws are detected when the transducer is perpendicular to the longitudinal axis of the pipe. To detect axial flaws, the transducer is rotated along the longitudinal axis of the pipe.

Figure 1:
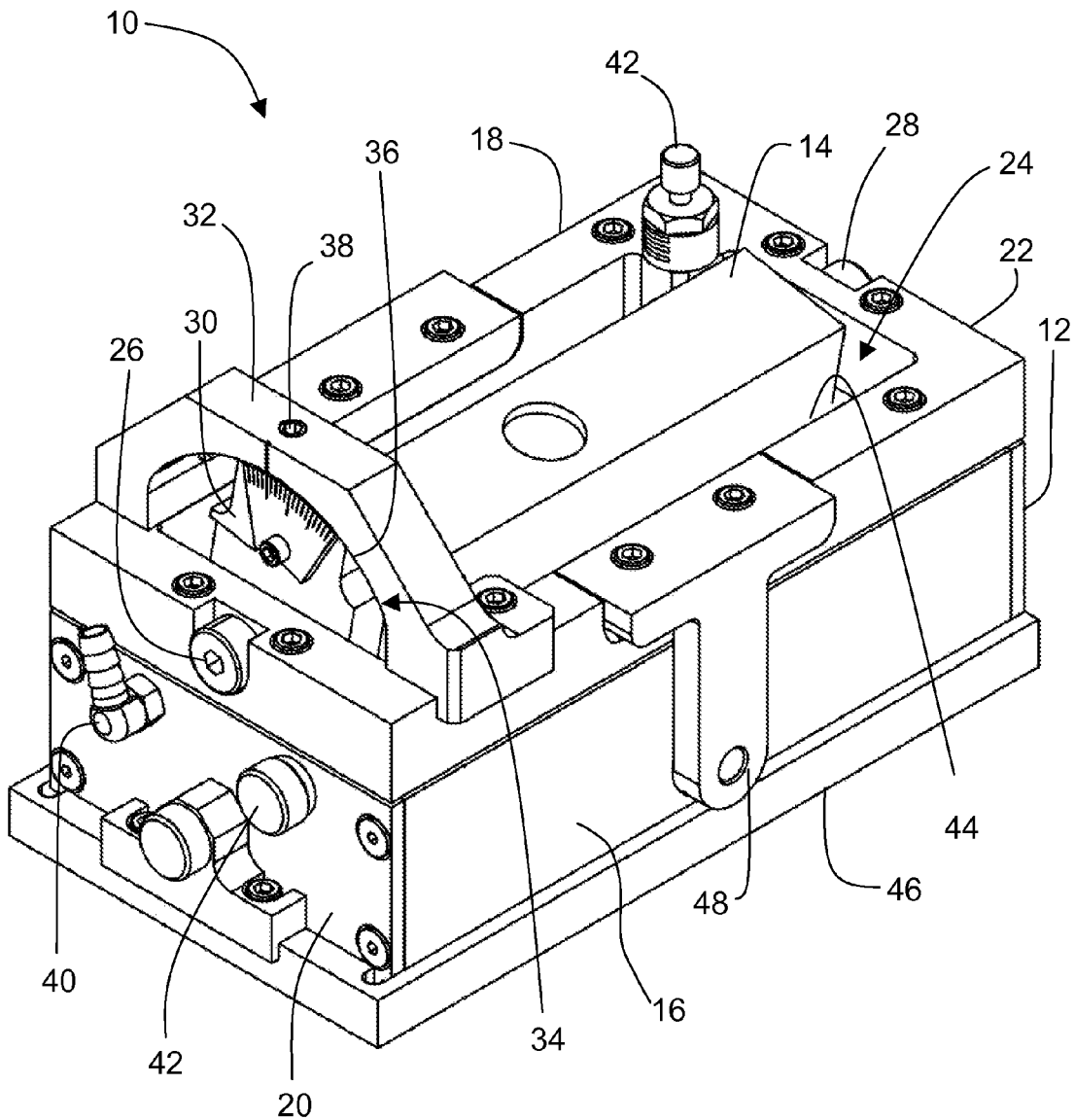
FIG. 1 is a perspective illustration of a phased array ultrasonic probe assembly in accordance with an embodiment of the present invention.

Referring to the drawings, FIG. 1 is a perspective illustration of a phased array ultrasonic probe assembly 10 in accordance with an exemplary embodiment of the present invention. Probe assembly includes a housing 12 and a phased array ultrasonic transducer 14 pivotably mounted in housing 12. Housing 12 is substantially rectangular shaped and includes a first side wall 16, an opposing second side wall 18, a first end wall 20, and an opposing second end wall 22. Side walls 16 and 18, and end walls 20 and 22 define a cavity 24 in which transducer 14 is mounted.

Transducer pivot pins 26 and 28 extend through end walls 18 and 20 respectively to pivotably mount transducer 14 in housing 12. An angle adjustment block 30 is coupled to one end of transducer 14 and interfaces with an angle selection member 32 coupled to housing 12. In the exemplary embodiment, angle selection member 32 includes an arcuate portion 34 that mates to an arcuate shaped end 36 of angle adjustment block 30. A set screw 38 in angle selection member locks angle adjustment block 30 in place thereby setting the desired angle of transducer 14.

Housing cavity 24 is filled with a liquid. In the exemplary embodiment, the liquid is water, and in another embodiment, the liquid is a combination of liquids that facilitate the transmission and reception of ultrasonic sound beams. A fluid inlet 40 is located in housing 12 to permit the filling of housing cavity 24 with fluid. Housing 12 also includes at least one air release vent 42 (two shown) to remove any air trapped in cavity 24 during the filling of cavity 24 with a fluid.

A first flexible membrane seal 44 covers the area between transducer 14 and side walls 16 and 18 to hold the fluid inside housing cavity 24. A second seal 46 seals the bottom of housing 12 with the object that is being inspected. Seal 46 in one embodiment is a membrane seal having at least one slit or opening to permit the fluid to flow through housing cavity 24 while maintaining a volume of fluid in housing cavity 24 that fills the volume of cavity 24 between the bottom of transducer 14 and the object that is being examined. In an alternate embodiment, seal 46 is a resilient material that is located around the bottom edge of housing 12 to provide a watertight seal so that the liquid cannot drain out of housing cavity 24. Housing 12 also includes at least one tool manipulator attachment member 48 to couple probe assembly 10 to a tool manipulator (not shown)

Figure 2:
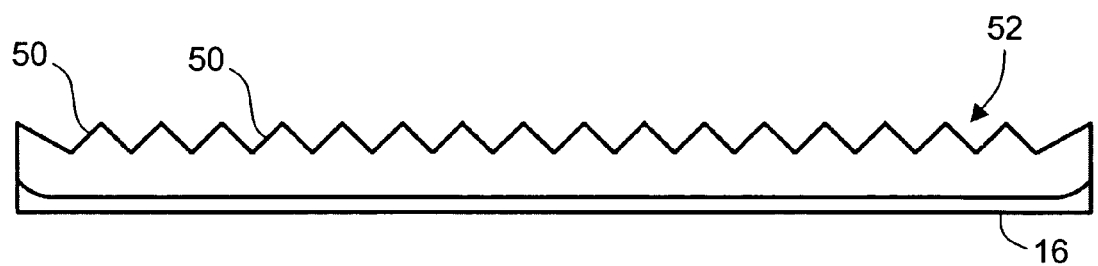
FIG. 2 is a sectional illustration of a side wall of the phased array ultrasonic probe assembly shown in FIG. 1.
Figure 3:
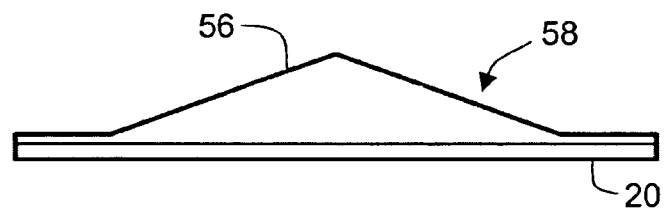
FIG. 3 is a sectional illustration of an end wall of the phased array ultrasonic probe assembly shown in FIG. 1.

FIG. 2 is a sectional illustration of side wall 16 of phased array ultrasonic probe assembly 10, and FIG. 3 is a sectional illustration of end wall 20. Referring also to FIGS. 2 and 3, side walls 16 and 18 include a plurality of projections 50 extending from inner surfaces 52 and 54 respectively. End walls 20 and 22 include at least one projection 56 extending from inner surfaces 58 and 60 respectively. In the exemplary embodiment, projections 50 and 56 have a triangle or "saw tooth" shape. In alternate embodiments, projections 50 and 56 can have other shapes, for example, semi-circular, elliptical, or any other shape that reduces noise produced by the sound waves bouncing off the walls of housing 12.

Figure 4:
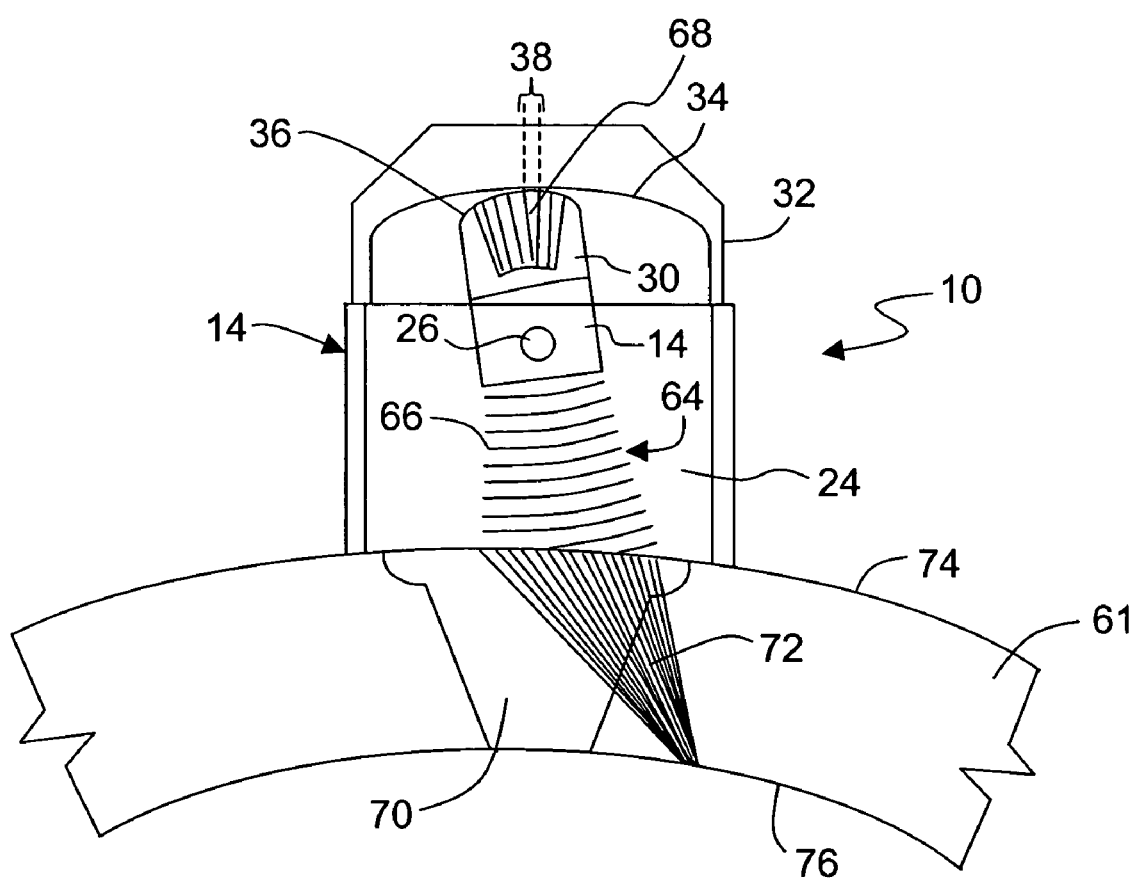
FIG. 4 is a side illustration of the phased array ultrasonic probe assembly shown in FIG. 1 mounted on a pipe.
Figure 5:
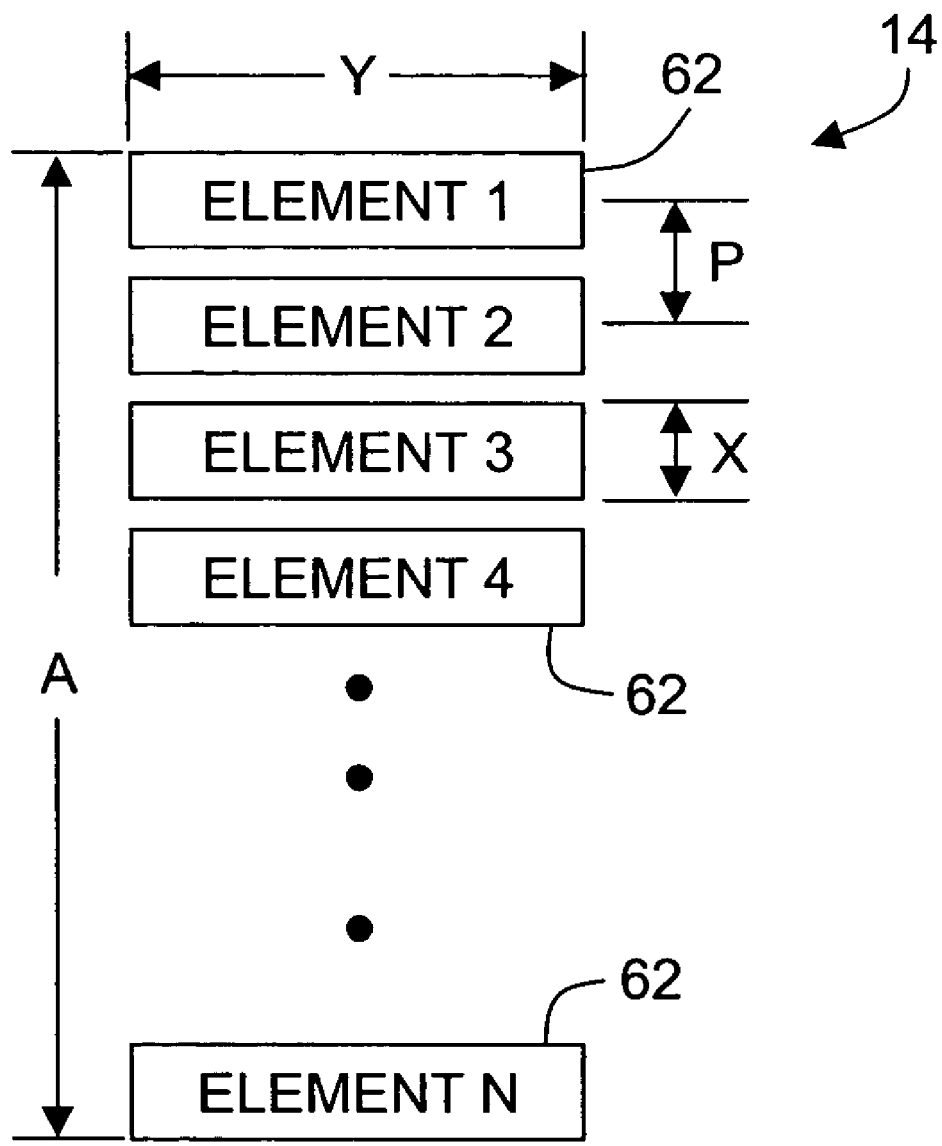
FIG. 5 is a schematic illustration of the phased array ultrasonic transducer shown in FIG. 1.

FIG. 4 is a schematic illustration of phased array transducer probe assembly 10 mounted on a pipe 61, and FIG. 5 is a schematic illustration of phased array ultrasonic transducer 12. Referring also to FIGS. 4 and 5, transducer 12 includes a plurality of elements 62 that emit ultrasonic beam 64. An important aspect of probe assembly 10 usage is the ability to dynamically synthesize ultrasonic beam 64 and create a "Virtual Probe" of any angle within the overall beam spread of an individual element 62. During operation, beam 64 is created by sequentially firing each element 62 to create a wave front 66 following a desired angle 68. Angle 68 is selected and set up by angle selection member 32 and angle adjustment block 30. This "Virtual Probe" can also be "swept" through a weld 70 in pipe 61 by firing groups of elements in a large array. This effect can be used to dynamically focus or "electrically steer" ultrasonic beam 64 by selecting the probe firing order and pulse delays. This can be changed on a pulse by pulse basis to effectively "sweep" a focal point through weld 70. Beam steering and dynamic focusing can be combined to enable resultant beam 64 to be both focused and angled in predetermined increments. Ultrasonic phased array transducers 14 are commercially available from Krautkramer Ultrasonic Systems Group of Agfa NDT, Inc., Lewistown, Pa.

Referring to FIG. 5, the basic parameters of transducer 14 are defined as frequency, aperture A, element size X, element width Y, pitch P, and number of elements 62. A suitable frequency is 1.0 to 5.0 MHz for the material type and thickness of weld 70 in pipe 61 located in a nuclear reactor. However, other transducer frequencies can be used for pipes and pipe welds manufactured from other materials.

Element pitch P is determined by calculating the acoustic aperture A needed to focus beam 64 at the required sound path and dividing this value by the total number of elements 62 and the amount of steering needed to create the desired angles. The size X of elements 62 is set as the maximum possible pitch. The width Y of elements 62 is determined by calculating the effective diameter for a near field of fifteen centimeters to give the smallest beam profile in the y-plane. The physical restrictions of the scanning surface must also be considered in determining the basic parameter values of transducer 14.

Referring again to FIG. 4, a volume 72 of beam 64 that is examined includes weld 70 and pipe 61 extending from outer surface 74 towards inner surface 76. Just as transducer 14 can be oriented in a plurality of angles 68, as discussed above, beam 64 can be oriented or steered in plurality of angles. In one embodiment, beam 64 can be steered along a substantially axial path across weld 70 in a linear path in the orientation of weld 70. In another embodiment, beam 64 can be steered along a substantially axial path across weld 70 in a linear path perpendicular to the orientation of weld 70 in predetermined increments. In yet another embodiment, beam 70 can be steered along a substantially circular path across weld 70.

While the invention has been described in terms of various specific embodiments, those skilled in the art will recognize that the invention can be practiced with modification within the spirit and scope of the claims.

What is claimed is:

1. A phased array ultrasonic probe assembly comprising:
   a housing; and
   a phased array transducer supported inside said housing; said housing comprising:
   a first side wall and an opposing second side wall;
   a first end wall and an opposing second end wall, said first and second side walls and said first and second end walls defining a housing cavity in which said phased array transducer is positioned;
   a first flexible seal to seal a top of said housing cavity; and
   a second flexible seal to seal a bottom of said housing cavity;
   said first and said second side walls each having an inside surface comprising a plurality of projections.

2. A phased array ultrasonic probe assembly in accordance with claim 1 wherein said first and said second end walls each have an inside surface comprising at least one projection.

3. A phased array ultrasonic probe assembly in accordance with claim 2 wherein said at least one projection of said first and said second end walls comprise an angled shaped projection.

4. A phased array ultrasonic probe assembly in accordance with claim 3 wherein said at least one angled shaped projection comprises a triangularly shaped projection.

5. A phased array ultrasonic probe assembly in accordance with claim 1 wherein said first and second side wall projections comprise angled projections.

6. A phased array ultrasonic probe assembly in accordance with claim 5 wherein said plurality of angled projections comprise a plurality of saw tooth shaped projections.

7. A phased array ultrasonic probe assembly in accordance with claim 1 wherein said phased array transducer is pivotably mounted in said housing.

8. A phased array ultrasonic probe assembly in accordance with claim 1 wherein said housing further comprises a fluid inlet.

9. A phased array ultrasonic probe assembly in accordance with claim 1 wherein said housing further comprises at least one vent.

10. A phased array ultrasonic probe assembly comprising:
    a housing; and a phased array transducer pivotably mounted inside said housing, said phased array transducer comprising a plurality of elements, said housing comprising:
a first side wall and an opposing second side wall;
a first end wall and an opposing second end wall, said first and second side walls and said first and second end walls defining a housing cavity in which said phased array transducer is positioned;
a first flexible seal to seal a top of said housing cavity; and
a second flexible seal to seal a bottom of said housing cavity;
said first and said second side walls each having an inside surface comprising a plurality of projections.

11. A phased array ultrasonic probe assembly in accordance with claim 10 wherein said first and said second end walls each have an inside surface comprising at least one projection.

12. A phased array ultrasonic probe assembly in accordance with claim 11 wherein said at least one projection comprises a triangularly shaped projection.

13. A phased array ultrasonic probe assembly in accordance with claim 10 wherein said plurality of projections comprise a plurality of saw tooth shaped projections.

14. A phased array ultrasonic probe assembly in accordance with claim 10 wherein said housing further comprises a fluid inlet.

15. A method of inspecting a portion of a weld in a metal object using a phased array ultrasonic probe assembly, the probe assembly comprising a housing and a phased array transducer pivotably mounted inside the housing, the housing comprising a first side wall and an opposing second side wall, and a first end wall and an opposing second end wall, the first and second side walls and the first and second end walls defining a housing cavity in which the phased array transducer is positioned, the first and second side walls each having an inside surface comprising a plurality of projections, the housing further comprising a first flexible seal to seal a top of said housing cavity, and a second flexible seal to seal a bottom of said housing cavity, said method comprising:
positioning the phased array ultrasonic probe assembly adjacent an outer surface of the portion of the weld to be inspected;
adding a fluid to the housing cavity; and
scanning the weld.

16. A method in accordance with claim 15 wherein the housing further comprises a fluid inlet, said adding a fluid to the housing cavity comprises flowing a fluid through the fluid inlet and into the housing cavity.

17. A method in accordance with claim 15 wherein said adding a fluid to the housing cavity comprises adding a fluid to the housing cavity so that the fluid fills the volume between a bottom surface of the phased array transducer and the outer surface of the weld.

18. A method in accordance with claim 15 further comprising pivoting the phased array transducer through a plurality of angles and scanning the weld at each transducer angle.

* * * * *